United States Patent
Aikins et al.

(10) Patent No.: US 6,372,936 B1
(45) Date of Patent: Apr. 16, 2002

(54) OPTICAL RESOLUTION OF AMINOISOBOBUTYRIC ACID

(75) Inventors: James Abraham Aikins, Pendleton; Tony Yantao Zhang, Indianapolis, both of IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/566,883

(22) Filed: May 8, 2000

Related U.S. Application Data

(60) Provisional application No. 60/138,312, filed on Jun. 9, 1999, and provisional application No. 60/168,349, filed on Dec. 1, 1999.

(51) Int. Cl.[7] ................ C07C 229/00; A61K 38/00
(52) U.S. Cl. ............... 560/155; 562/401; 514/9; 514/11
(58) Field of Search ............ 560/155; 562/401; 514/9, 11

(56) References Cited

U.S. PATENT DOCUMENTS 5,952,298 A * 9/1999 Moore et al. ............... 514/9

FOREIGN PATENT DOCUMENTS

| WO | WO 9640184 | * | 12/1996 |
| WO | WO 9808505 | * | 3/1998 |

OTHER PUBLICATIONS

Russell A. Barrow, et al., Total Synthesis of Cryptophycins. Revision of the Structures of Cryptophycins A and C. *J. Am. Chem. Soc.* (1995), 117, pp. 2479–2490.

Charles R. Roe, et al., Methylmalonic Semialdehyde Dehydrogenase Deficiency: Psychomotor Delay and Methylmalonic Aciduria Without Metabolic Decompensation *Molecular Genetics and Metabolism* 65, pp. 35–43 (1998) Article No. GM982737.

Rabindra Rej, et al., Total Synthesis of Cryptophycins and Their 16–(3–Phenylacryloyl) Derivatives *J. Org. Chem.* 1996, 61, pp. 6289–6295.

E. Juaristi, et al., Rabindra Rej, et al. Enantioselective Synthesis of β–Amino Acids–VII, pp. 2238–2246.

Tamaki, Nanaya, *Biochim. Biophys Acta* (1990), 1035 (1), pp. 117–19.

M. Akssira, *Amino Acids* (1994), 7(1), pp. 79–81.

* cited by examiner

*Primary Examiner*—Ralph Gitomer
*Assistant Examiner*—Devesh Khare
(74) *Attorney, Agent, or Firm*—Robert D. Titus

(57) ABSTRACT

A process for resolving amino protected racemic 3-amino-2-methylpropionic acid which comprises the steps of: (1) reacting said amino protected acid with a protected amino group with an enantiomer of a chiral amine to form diastereomeric salts; (2) recrystallizing the diastereomeric salts from ethyl acetate to separate the diastereomeric salts into crystal fractions; and (3) releasing the resolved acid from the diastereomeric salt by treating the diastereomeric salt with a basic solution is disclosed. A process for the preparation of the cryptophycin molecules is also disclosed.

15 Claims, No Drawings

OPTICAL RESOLUTION OF AMINOISOBOBUTYRIC ACID

CROSS-REFERENCE TO RELATED APPLICATION

This application claims priority to provisional application Ser. No. 60/138,312 filed Jun. 9, 1999 and provisional application Ser. No. 60/168,349 filed Dec. 1, 1999.

BACKGROUND OF THE INVENTION

Aminoisobutyric acid (3-amino-2-methylpropionic acid) is a chiral molecule and exists in the form of the (R) and the (S) enantiomers. (R) (–) Aminoisobutyric acid is a useful intermediate in the convergent synthesis of cryptophycin molecules; see for example, Barrow, R. A., et. al, J. Am. Chem. Soc. 117, 2479–2490 (1995). Accordingly, aminoisobutyric acid, for use in the synthesis of cryptophycin, must be synthesized in a chiral form, or synthesized as a racemic molecule and resolved.

Cryptophycins are potent tumor-selective cytotoxins which are elaborated by terrestrial blue green algae. They show excellent activity against solid tumors implanted in including drug resistant tumors, and are thus useful as anti-cancer agents. Cryptophycins were originally isolated from blue green algae. However, they have now been synthesized using a convergent synthesis in which the cryptophycin molecule is put together from four sub-units, named in the literature A, B, C and D. For one group of cryptophycins, the C Unit is R(–)aminoisobutyric acid. Barrow (J. Am. Chem. Soc., 117, 2479–2490 (1995)) reports a synthesis of (R) (–)3-amino-2-methylpropionic acid beginning with the chiral molecule, methyl(S)-(+)-3-hydroxy-2-methylpropanoate which is a rather expensive starting material. The synthesis begins with the ammonolysis of the propanoate ester at 50° C. in a sealed tube for one week. The ammonolysis could be speeded up through the use of 10% sodium cyanide as a catalyst. However, the cyanide catalyst is difficult to remove from the reaction product. In the next step, the amide is reduced with borane to produce an amino alcohol. After protection of the amine, the alcohol is oxidized with ruthenium tetraoxide to give the desired carboxylic acid. This is a complex and expensive synthesis.

A more recent synthesis (Rabida, Res, et al., J. Org. Chem. 61, p.6289(1996)) starts with S-(+)-3-bromo-2-methyl-1-propanol, and produces the desired acid in 70% yield. However, S-(+)-3-bromo-2-methyl-1-propanol is an expensive starting material.

The (S) enantiomer of aminoisobutyric acid occasionally shows up in human serum and urine; see for example, Row, Charles R., et al. MOL. GENET. METAB. (1998), 65 (1, 35–43); Tamaki, Nanaya, Biochim. Biophys. Acta (1990), 1035 (1) 117–19. The pure (S) enantiomer of aminoisobutyric acid may be used as an analytical standard in metabolic studies. Several elegant and expensive synthesis have been reported for the (S) enantiomer of aminoisobutyric acid. Eusedio, Juaristi, et al. (Tetrahedron: Asymmetry (1996), 7(8), 2233–2246) report a synthesis from 1-benzoyl-2 (S)-tert-butyl-3-methylperhydropyrimidin-4-one. M. Akssira (Amino Acids (1994), 7 (1), 79–81) reports the synthesis using the β-alanine derivative with two chiral handles.

BRIEF SUMMARY OF THE INVENTION

The present invention provides the process for resolving racemic 3-amino-2-methylpropionic acid. The amino group of the acid is protected, and the protected acid is reacted with a chiral amine to form diastereomeric salts. The diastereomeric salts are recrystallized from ethyl acetate to separate the salts into pure fractions. The protected acid is recovered from the purified diastereomeric salts by treatment with base, and the amine-protecting group is removed with treatment with a strong mineral acid solution.

DETAILED DESCRIPTION OF THE INVENTION

The present invention provides a simple and economical method for resolving racemic aminoisobutyric acid into the (S) and (R) enantiomers. A convenient synthesis of racemic aminoisobutyric acid is also disclosed.

A Convenient Synthesis of Racemic Aminoisobutyric Acid

For the purposes of the present invention, the racemic aminoisobutyric acid may be synthesized by any convenient method. Such methods are known to those skilled in the art and the racemic acid produced by any method may be readily resolved by the method of this invention. A convenient synthesis of racemic aminoisobutyric acid begins with ethyl 2-cyanopropionate. The cyano portion of the molecule is reduced to an amine with hydrogen gas and a catalyst, to form the ethyl ester of the amino acid. The amino group is protected, and the ester is cleaved to form the amino protected amino carboxylic acid.

Ethyl-2-cyanopropionate may be obtained by careful hydrogenation of ethyl-2-cyanoacrylate, which is readily available and often used as a glue. Ethyl-2-cyanopropionate is reacted with hydrogen in the presence of a hydrogenation catalyst in a suitable solvent such as 1,4 dioxanq, THF, t-butyl-methyl ether. The preferred solvent is THF. The mixture is heated to reflux and subjected to hydrogenation at a moderate pressure in the range of 40–70 pound psia (absolute pressure). Suitable hydrogenation catalysts include platinum, platinum on charcoal, platinum oxide, ranoy nickel and various rhodium catalysts. The preferred catalyst is 5% rhodium on alumina.

It is preferred to conduct the hydrogenation in the presence of a amine protective reagent to protect the amine as it is being formed. Among the protective groups that can be used include BOC (t-butyloxycarbonyl), carbobenzyloxy, phenoxyacetyl, 2,2,2-trichloro-1,1-dimethylethylcarbonyl, and 2,2,2-trichloroethoxycarbonyl. Other suitable protective groups are well known to those skilled in the art. See, for example, *Protective Groups in Organic Synthesis*, Greene, Theodora W., 1931, $3_{rd}$ ed./Theodora W. Greene and Peter G. M. Wuts, New York: Wiley, c1999. After the hydrogenation is complete (in approximately 18–24 hours), the solution is concentrated by the removal of solvent. Water, and a strong inorganic base are added to cause the hydrolysis of the ester portion of the molecule. Suitable inorganic bases include lithium hydroxide, sodium hydroxide, sodium carbonate, potassium hydroxide and potassium carbonate. Finally, the entire mixture is neutralized with a suitable acid including inorganic acids such as hydrochloric acid, sulfuric acid, phosphoric acid or a simple inorganic acid such as acetic acid, and the amino protected-aminoisobutyric acid is extracted with a solvent and isolated as a low-melting waxy solid. One advantage of conducting the hydrogenation process in the presence of a protective group is that it yields the aminoisobutyric acid with the amino group already protected. If one synthesizes aminoisobutyric acid by some other route in which the acid is formed without a protective group on the amine, it is important that the amine be protected before the resolution step.

Resolution of Racemic Aminoisobutyric Acid

The resolution is accomplished by first placing a blocking group or protective group on the amine group of amino isobutyric acid and then by reacting the carboxylic acid group of the amino blocked aminoisobutyric acid with a chiral amine to form diastereomeric salts. Obviously, the amine portion of the aminobutyric acid must be protected so that it will not compete with the reaction between the chiral amine and the carboxylic acid. Suitable amines for reaction with the acid portion of the aminoisobutyric acid include (α-methyl-benzylamine, quinine (the (R) enantiomer of β-methoxycinchonan-9-ol) and quinidine (the (S) enantiomer of β-methoxycinchonan-9-ol). The preferred amine is (α-methyl-benzylamine. Either enantiomer of the amine may be used. The reaction and resolution process using either enantiomer of a chiral amine is illustrated in Scheme II. In this scheme, the enantiomer for the acid is shown in bold face standard type, and the enantiomer for the amine is shown in italics. The (RR) salts and the (SS) salt have higher melting points than the (RS) and the (SR) salts. For α-methyl-benzylamine, the (RR) and (SS) salts melt at 133° C. while the (RS) and (SR) salts melt at 119° C.

Several solvents were tested for the selective crystallization of the diastereomeric salts. These solvents included ethanol, methanol, THF, t-butylmethyl ether, isopropyl alcohol, and combinations of these solvents. None of these solvents provided the desired separation of the diastereomeric salts.

Surprisingly, it was found that in ethyl acetate, the (RR) and (SS) salts were substantially less soluble than the (RS) and the (SR) salts. When the mixture diastereomeric salts is dissolved in ethyl acetate, the (RR) salt or (SS) salt (depending upon the enantiomer of the amine which has been selected) precipitates at approximately 40° C. This precipitate is collected, and the filtrate is cooled at approximately 25° C. the (SR) or (RS) salts (depending upon the enantiomer of the amine selected) precipitates.

The precipitated salts are enriched in a preferred enantiomer of the acid. Thus, if the (S) enantiomer of the amine is selected, the high temperature precipitate will be enriched in the (S) enantiomer of the acid. The low temperature precipitate will be enriched in the (R) enantiomer of the acid. If the (R) enantiomer of the amine is selected, then the high temperature precipitate will be enriched in the (R) enantiomer of the acid, and the low temperature precipitate will be enriched in the (S) enantiomer of the acid. The first recrystallization from ethyl acetate produces crystal fractions having ratios of 2:1 in favor of the preferred diasteriomeric salt. Further recrystallizations may be done to produce crystal fractions having the desired level of purity. An enantiomeric purity of 95% is achieved with four recrystallizations.

The racemic 3-amino-2-methylpropionic acid, with an appropriate block for the amine group may be reacted with either the (R) or (S) enantiomer of the selected amine. If one selects the (R) enantiomer, the isolation of the (R) acid will be somewhat easier since the (RR) diastereomeric salt precipitates from the solution before the (RS) diastereomeric salt. One can isolate both the (RR) and the (RS) diastereomeres and selectively recrystallize each one thereby obtaining the two diastereomeric salts at the desired level of purity.

By treating each diastereomeric salt with a solution of an inorganic base such as alkali metal carbonate or hydroxide, or alkaline earth carbonates and hydroxides, one can cause disassociation of the salts, and thereby recover both the (R) and the (S) enantiomers of the acid. However, it is often easier to recrystallize higher melting crystals, that is, the (RR) diastereomeric salt or the (SS) diastereomeric salt. Accordingly, if one desires only one enantiomer of 3-amino-2-methylpropionic acid, it is preferred to start with an amine of the same stereoisomeric family as the desired enantiomer of the acid. Thus, if one desires the (R) enantiomer of the acid, it is preferred to form the diastereomeric salts from an (R) amine. Similarly, if the (S) enantiomer of the acid is desired, it is preferred to form the diastereomeric salts from an S amine.

The acid may be recovered from the amine protected acid by dissolving the amine protected in a suitable solvent such as methylene chloride, and washing the solution with an aqueous mineral acid solution such as 1N hydrochloric acid, 1N sulfuric acid, and 1N phosphoric acid.

EXAMPLE 1

Preparation of 3-[(tert-Butoxycarbonyl)amino]-2-methylpropionic acid

A 5.0 liter stainless steel autoclave was charged with 5% rhodium on alumina (46.08 g), BOC anhydride (151.22 g, 0.693 moles), ethyl-2-cyanopropionate (80.0 g, 0.630 moles) and THF (2.5 liters). The reaction mixture was stirred and subjected to a hydrogen pressure of 55 psia at THF reflux temperature. A proton NMR of an aliquot sample after 18 hours indicated the reaction was complete. The reaction mixture was then allowed to equilibrate to room temperature, vented and purged with nitrogen. The reaction mixture was filtered over hyflo and concentrated in vacuo to give a solution of mass 645.0 grams. To this solution was added water (0.5 liter) and KOH (70.69 g, 1.26 moles). The two-phase reaction mixture was then heated at THF reflux temperature for 18 hours to form a homogeneous solution. The solution was cooled to room temperature and the pH was adjusted to 3.0 with 85% phosphoric acid (192.0 ml). The neutralization temperature was maintained at 30° C. by controlling the rate of addition of the phosphoric acid (addition time=2.0 hours.) The organics were then extracted with t-butylmethyl ether (0.5 liter). The ether solution was dried with anhydrous $MgSO_4$, filtered, and concentrated in vacuo to an oil which solidified to a waxy low melting solid (mass=91.6 grams, ~72.0% wt. yield). $^1$H NMR ($CDCl_3$, 300 MHz) δ1.15 (d, J=7.1 Hz, 3H), 1.4 (s, 9H), 2.6 (m, 1H), 3.2 (m, 2H), 5.09 (bs, 0.73H), 6.19 (bs, 0.27H), 9.2 (bs, 1H); $^{13}$C NMR ($CDCl_3$, 300 MHz) δ180.55, 155.93, 79.60, 42.75, 40.08, 28.41, 14.70. IR ($CHCl_3$) 3457, 2982, 1709, 1508, 1368, 1243, 1168 $cm^{-1}$. MS{$FD^+$} m/z (relative intensity) 204.0. Anal. Calcd. For $C_9H_{17}N_1O_4$: C, 53.19; H, 8.43; N, 6.89. Found: C, 53.14; H, 8.40; N, 6.73.

EXAMPLE 2

Resolution of 3-[(tert-Butoxycarbonyl)amino]-2-methylpropionic acid with (R)-(+)-α-methylbenzylamine.

To a solution of 3-[tert[Butoxycarbonyl)amino]-2-methylpropionic acid (202.4 g, 0.99 moles) in ethyl acetate (0.7 liters), at room temperature, was added (R)-(+)-α-methylbenzylamine (127.0 ml), all at once, with vigorous mechanical stirring. The reaction exothermed to 47° C. by the end of the addition of the resolving agent. A massive white precipitate of the diastereomeric salt formed as the reaction mixture cooled to 42° C. The reaction mixture was stirred and allowed to cool to room temperature. The solution was filtered and the precipitate was collected and dried under vacuum (mass=278.9 g). The precipitate was redissolved in hot ethyl acetate (0.80 liters) and allowed to equilibrate to 34° C. The solution was filtered and the precipitate was collected, the re-crystallization was repeated with 0.5 liters, 0.35 liters and 0.30 liters of hot ethyl acetate to afford, after drying, 49.79 grams of diastereomeric salt. A sample of this salt was subjected to a 1N HCl acid wash in CH$_2$Cl$_2$. The organic layer was separated, dried with anhydrous MgSO$_4$, filtered and concentrated to an oil in in vacuo. This oil was (R) 3-[tert-[Butoxycarbonyl) amino]-2-methylpropionic acid. Analysis of oil gave the following results: ee=95.0%; optical rotation=−17.9°; % weight yield based on theory=62.34%). $^1$H NMR (CDCl$_3$, 300 MHz) δ1.15(d, J=7.1 Hz, 3H), 1.4 (s,9H), 2.6 (m,1H), 3.2 (m, 2H) 5.09 (bs, 0.73H) 6.19 (bs, 0.27H), 9.2 (bs, 1H); $^{13}$C NMR (CDCl$_3$, 300 MHz) δ 180.55, 155.93, 79.60, 42.75, 40.08, 28.41, 14.70. IR (CHCl$_3$) 3457, 2982, 1709, 1508, 1368, 1243, 1168 cm$^{-1}$. MS{FD$^+$} m/z (relative intensity) 204.0. Anal. Calcd. For C$_9$H$_{17}$N$_1$O$_4$: C, 53.19; H, 8.43; N, 6.89. Found: C, 53.14; H, 8.40; N, 6.73.

Scheme 1

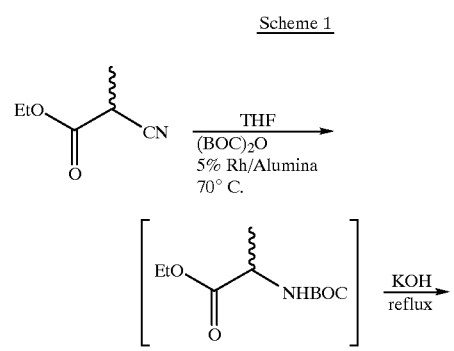

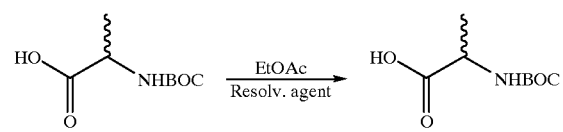

Scheme 2
Resolution Process Flow for BOC-aminoisobtyric acid

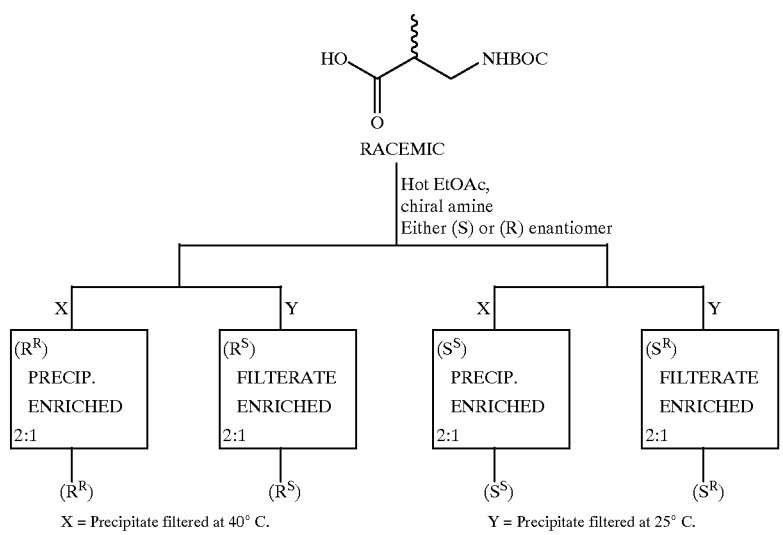

X = Precipitate filtered at 40° C.   Y = Precipitate filtered at 25° C.

PREPARATION OF CRYPTOPHYCIN MOLECULES

Cryptophycin molecules are synthesized using a convergent synthesis in which the cryptophycin molecules are put together from four (4) sub-units. These have been named in the literature as A, B, C, and D. For one group of cryptophycin, the C Unit is R(−)aminoisobutyric acid. Methods of synthesizing cryptophycin molecules are well known in the art. For example, the following publications disclose synthesis of sub-units or total syntheses:

J. Med. Chem. (1999), 42(14), 2588–2603.
Bioorg. Med. Chem. Lett. (1999), 9(3), 369–374.
J. Org. Chem. (1999), 64(5), 1459–1463.
Bioorg. Med. Chem. Lett. (1999), 9(1), 69–74.
Tetrahedron Lett. (1998), 39(48), 8771–8774.
Tetrahedron Lett. (1998), 39(46), 8405–8408.
Tetrahedron: Asymmetry (1998), 9(16), 2777–2781.
J. Org. Chem. (1998), 63(15), 5288–5294.
Tetrahedron Lett. (1997), 38(10), 1703–1706.
J. Org. Chem. (1996), 61(20), 6893–6900.
J. Org. Chem. (1996), 61(18), 6289–6295.
Bioorg. Med. Chem. Lett. (1996), 6(10), 1111–1116.
J. Am. Chem. Soc. (1995), 117(9), 2479–90.
WO 98/09988 A1   WO 98/0805   WO 98/08506
WO 98/09601 A2   WO 97/07798   WO 98/08812
WO 96/40184 A1   WO 97/23211   WO 97/31632

These references are incorporated by reference for their disclosure of the synthesis of cryptophycin molecules.

The A Fragment which goes into the cryptophycin synthesis is shown in the following formula:

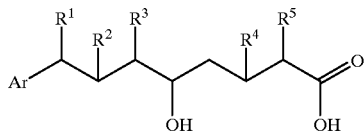

Ar is selected from the group consisting of phenyl, any unsubstituted aromatic, substituted aromatic, unsubstituted heteroaromatic group, substituted heteroaromatic group, heterocyclic, $(C_1-C_{12})$ alkyl, $(C_2-C_{12})$ alkenyl, $(C_2-C_{12})$ alkynyl. $R^1$ and $R^2$ are each independently selected from the group consisting of halogen, monalkylamino, dialkylamino, trialkylammonium, alkylthio wherein the alkyl groups are $(C_1-C_7)$ alkyl groups, $OR^{31}$, $SR^{31}$, or $R^{32}$—N—$R^{31}$ where $R^{31}$ and $R^{32}$ are independently H or $(C_{1-C6})$ alkyl; or

- $R^1$ and $R^2$ may be taken together with C-18 and C-19 to form an epoxide ring, an aziridine ring, an episulfide ring, a cyclopropyl ring; or
- $R^1$ and $R^2$ may be taken together to form a second bond between C-18 and C-19;
- $R^3$ is a alkyl group;
- $R^4$ is H or OH;
- $R^5$ is H or OH;
- $R^4$ and $R^5$ may be taken together to form a second bond between $C_{13}$ and $C_{14}$;

The B Fragment is shown in the following formula:

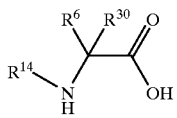

$R^6$ is a substituent selected from the group consisting of benzyl, hydroxybenzyl, alkoxybenzyl, halohydroxybenzyl, dihalohydroxybenzyl, haloalkoxybenzyl, or dihaloalkoxybenzyl group, unsubstituted heteroaromatic, substituted heteroaromatic, $(C_1-C_6)$ alkyl, substituted $(C_1-C_6)$ alkyl. $R^{30}$ is hydrogen or $(C_1-C_6)$ alkyl.

The D Fragment is shown in the following formula:

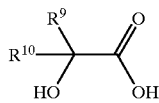

$R^9$ is selected from the group consisting of H, an alkyl group, alkenyl, alkynyl-$C_3$–$C_5$ cycloalkyl, and benzyl; $R^{10}$ is hydrogen or $(C_1-C_6)$ alkyl.

The C Fragment for this particular series of cryptophycins R(-)3-amino-2-methylpropanoic acid.

Starting from the C and D Fragments, the cryptophycin molecules are put together through the formation of ester and amide bonds. In forming these bonds, extensive use is made of blocking groups which protect various reactive sites from reaction as these bonds are formed. Appropriate protective groups may be selected by those skilled in the art. See, for example, *Protective Groups in Organic Synthesis*, Greene, Theodora W., 1931, 3rd ed./Theodora W. Greene and Peter G. M. Wuts, New York: Wiley, c1999.

A hydrocarbon group is a group formed from a hydrocarbon containing only carbon and hydrogen. $C_1$–$C_7$ as used herein, the term "alkyl" shall refer to a saturated, branched, cyclic or straight chain hydrocarbon group. The term "alkenyl" refers to a branched, cyclic or straight chain hydrocarbon group, having from one to three carbon-carbon double bonds. The term "alkynyl" refers to any branched, cyclic or straight chain hyydrocarbon group, as defined above, having at least one carbon-carbon triple bond.

As used herein, the term "substituted alkyl" refers to an alkyl group having one to three (inclusive) substituents selected from the group consisting of F, Cl, Br, I, $OR^{31}$, $SR^{31}$, and $NR^{31}$, $R^{32}$.

As used herein, the term "alkoxybenzyl" refers to a benzyl group having a $C_1$–$C_7$ alkoxy substituent at any available position on the benzyl ring. The alkoxy group is most preferable $(C_1-C_3)$ alkoxy. Methoxy is especially preferred. Accordingly, the term "haloalkoxybenzyl" refers to a benzyl group having a halo substituent in addition to an alkoxy substituent. Each halo or alkoxy group is substituted at any available carbon. Similarly, "halohydroxybenzyl" refers to a hydroxy substituted benzyl group that also has a halo substituent at any available carbon on the benzyl ring. Dihalohydroxybenzyl refers to a hydroxy substituted benzyl group that also has two halo substituents at any available carbon on the benzyl ring. Finally, the term "dihaloalkoxybenzyl" refers to an alkoxy substituted benzyl which additionally has two halo substituents each independently substituted to any available carbon on the benzyl ring.

As used herein, "unsubstituted aromatic group" refers to common aromatic rings having $(4n+2)\pi$ electrons in a moncyclic or bicyclic conjugated system. For example phenyl and naphthyl.

As used herein "substituted aromatic group" refers to an aromatic group substituted with a single group selected from the group consisting of halogen and $(C_1-C_7)$ alkyl group.

As used herein "unsubstituted heteroaromatic group" refers to an aromatic group which contain one or more non-carbon, atoms selected from the group consisting of oxygen, nitrogen, and sulfur, in the ring.

"Substituted heteraromatic" refers to a heteroaromatic group substituted with a single group selected from the group consisting of halogen and $(C_1-C_7)$ alkyl groups.

As used herein, "epoxide ring" means a three-membered ring whose backbone consists of two carbon atoms and an oxygen atom. As used herein, "aziridine ring" means a three-membered ring whose backbone consists of two carbon atoms and a nitrogen atom. As used herein "episulfide ring" means a three-membered ring whose backbone consists of two carbon and a sulfur atom. The methods of synthesizing cryptophycins, which are known in the art are illustrated in (Barrow, J. Am. Chem. Soc. 1995, 117, 2479–2490). Barrow by the method of Barrow combines the A and B sub-units and the C and D sub-units to form two units which he couples to form the final product. In Barrow's synthesis the A and B units are coupled using the following scheme:

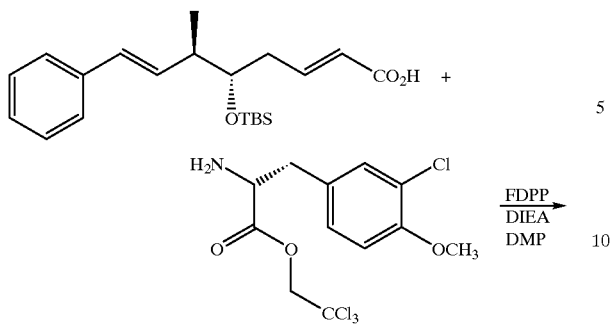

FDPP=(Pentafluorophenyl Diphenylphosphinate)
DIEA=(Diisopropylethylamine)
DMF=(N,N-dimethylformamide)
At a temperature of 25° C.

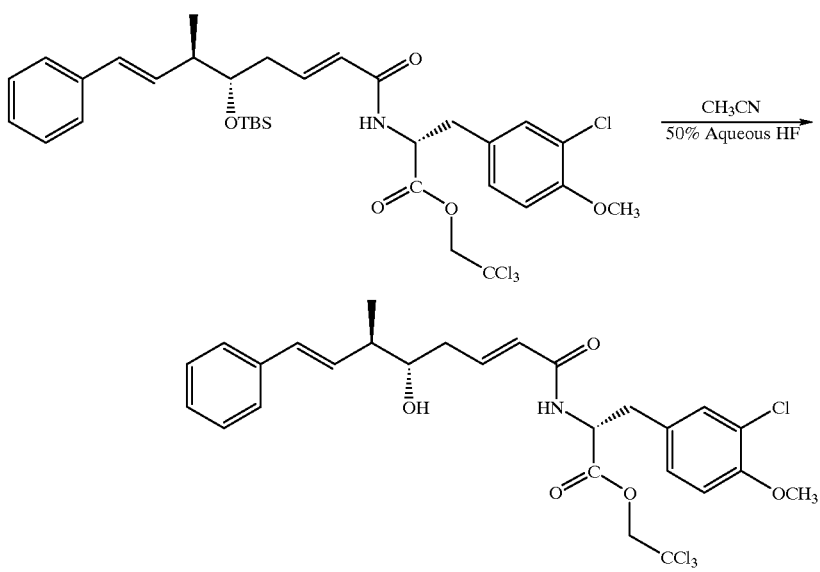

TBS=tert-butyldimethylsilyl ether

The C and D sub-units are coupled according to the following scheme:

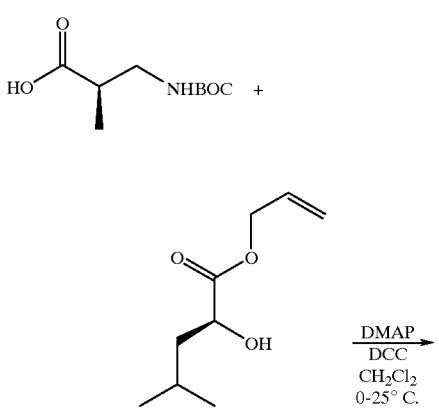

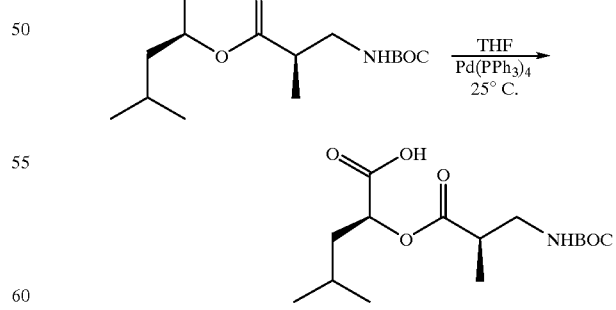

DMAP=(4-(dimethylamino) pyridine) THF=morpholine
DCC=(Dicyclohexylcarbodimide)

Finally, the total molecule is put together according to the following scheme:

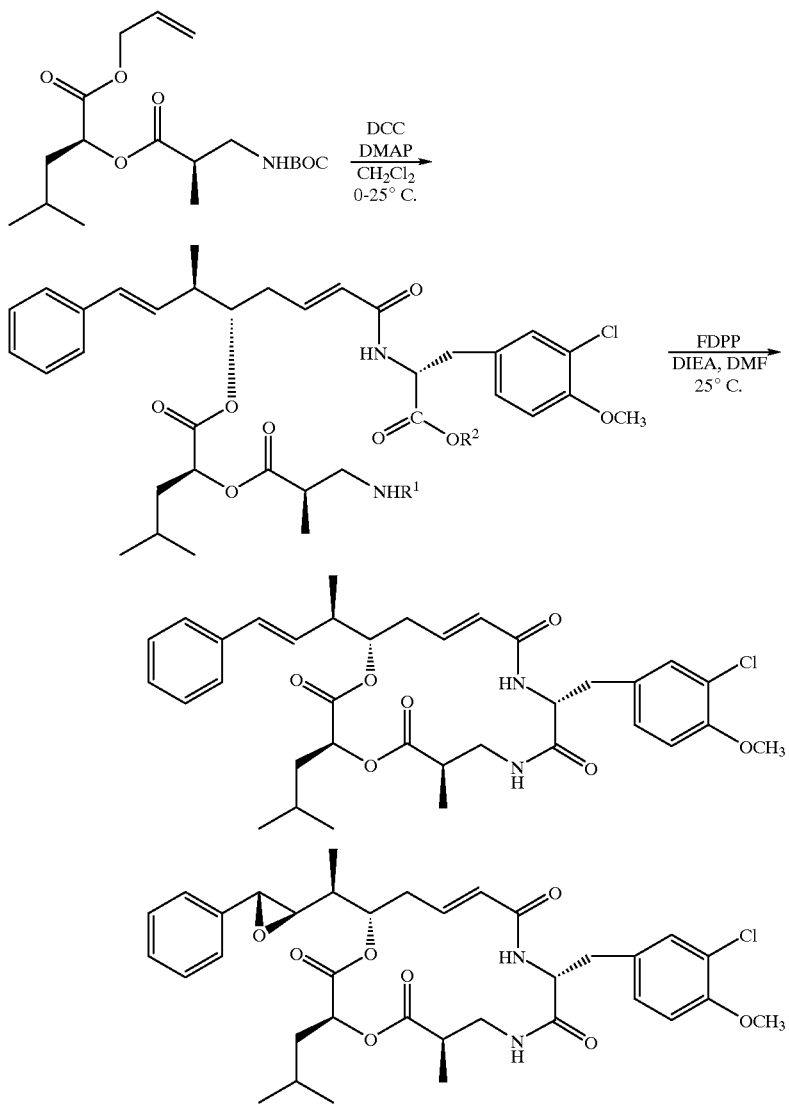

Formation of an epoxide at $R^1$ and $R^2$ may be accomplished by methods well known to those skilled in the art. Asymetric epoxidation methods are useful. One such method is the method of Shi disclosed in International Application WO 98/15544A1. In this method an olefin is asymmetrically epoxidated using a chiral ketone and an oxidizing agent. The epoxidation may be conducted as a final step in the synthetic scheme. On the other hand, it is often preferred to conduct the epoxidation on fragment A and synthesize the molecule with an A subunit in the form of the epoxide.

We claim:

1. A process for resolving amino protected racemic 3-amino-2-methylpropionic acid which comprises the steps of: (1) reacting said amino protected racemic 3-amino-2-methyl propionic acid with an enantiomer of a chiral amine to form diastereomeric salts; (2) recrystallizing the diastereomeric salts from ethyl acetate to separate the diastereomeric salts into crystal fractions; and (3) releasing the resolved acid from the diastereomeric salt by treating the diastereomeric salt with a solution of an inorganic base.

2. A process according to claim 1 for resolving racemic 3-amino-2-methylpropionic acid which comprises the additional step of reacting said racemic 3-amino-2-methylpropionic acid with a protective agent to form amino protected 3-amino-2-methylpropionic acid.

3. In a process for preparing a cryptophycin molecule by a convergent synthesis, in which (R) 3-amino-2-methylpropionic acid is a sub-unit; wherein the improvement comprises obtaining said (R) 3-amino-2-methylpropionic acid by a process according to claim 2.

4. A process according to claim 1 in which the chiral amine is (S) α-methyl-benzylamine.

5. A process according to claim 1 in which the chiral amine is (R) α-methyl-benzylamine.

6. A process according to claim 1 in which the chiral amine is quinine.

7. A process according to claim 1 in which the chiral amine is quinidine.

8. A process according to claim 1 further comprising the step of the treating the resolved amino protected 3-amino-2-methylpropionic acid with an aqueous mineralacid solution to remove the amine protective group thereby forming 3-amino-2-methylpropionic acid.

9. In a process for preparing a cryptophycin molecule by a convergent synthesis, in which (R) 3-amino-2- methylpropionic acid is a sub-unit; wherein the improvement comprises obtaining said (R) 3-amino-2-methylpropionic acid by a process according to claim 1.

10. A process for isolating the (R) ernantiomer of amino protected racemic 3-amino-2-methylpropionic acid comprising the steps of (1) reacting said acid with the (R) enantiomer of a chiral amine to form diastereomeric salts; (2) recrystallizing the diastereomeric salts from ethyl acetate to separate the diastereomeric salts into crystal fractions; and (3) releasing the resolved acid from the diastereomeric salt by treating the diastereomeric salt with a solution of an inorganic base.

11. A process according to claim 10 which the chiral amine is the (R) enantiomer of α-methylbenzylamine.

12. A process according to claim 10 in which the chiral amine is the (R) enantiomer of quinine.

13. A process for isolating the (S) enantiomer of amino protected racemic 3-amino-2-methylpropionic acid comprising the steps of (1) reacting said acid with the (S) enantiomer of a chiral amine to form diastereomeric salts; (2) recrystallizing the diastereomeric salts from ethyl acetate to separate the diastereomeric salts into crystal fractions; and (3) releasing the resolved acid from the diastereomeric salt by treating the diastereomeric salt with a basic solution.

14. A process according to claim 13 in which the chiral amine is the (R) enantiomer of α-methylbenzylamine.

15. A process according to claim 13 in which chiral amine is quinidine.

* * * * *